United States Patent [19]
Strike

[11] 3,959,363
[45] May 25, 1976

[54] 15-ETHYNYL-PGF$_{2\beta}$
[75] Inventor: Donald P. Strike, St. David, Pa.
[73] Assignee: American Home Products Corporation, New York, N.Y.
[22] Filed: Sept. 25, 1974
[21] Appl. No.: 509,173

[52] U.S. Cl. .................. 260/514 D; 260/267 R; 260/268 R; 260/293.65; 260/326.2; 260/468 D; 260/501.1; 260/501.15; 424/305; 424/317
[51] Int. Cl.$^2$ .................. C07C 61/38; C07C 69/74
[58] Field of Search .................. 260/468 D, 514 D

[56] References Cited
UNITED STATES PATENTS
3,804,890  4/1974  Bundy.............................. 260/514

FOREIGN PATENTS OR APPLICATIONS
2,364,706  7/1974  Germany

Primary Examiner—Robert Gerstl
Attorney, Agent, or Firm—Robert Wiser

[57]  ABSTRACT

Derivatives of PGF$_{2\beta}$ are prepared. These new compounds not heretofore found in nature possess various pharmacological activities, one of which is bronchodilation.

2 Claims, No Drawings

15-ETHYNYL-PFG$_{2\beta}$

BACKGROUND OF THE INVENTION

The prostaglandins are a group of hormone-like substances which may be viewed as derivatives of prostanoic acid. Several prostaglandins are found widely distributed in mammalian tissue and have been isolated from this source. Those prostaglandins have been shown to possess a variety of biological properties such as bronchodilation and the ability to reduce gastric secretion.

The present invention concerns PGF$_{2\beta}$ derivatives in which the 15-position (using the prostanoic acid numbering system) contains an ethynyl group, in addition to the normally present hydroxyl group. The preparation of 15-methyl PGF$_{2\beta}$ and 15-ethyl-PGF$_{2\beta}$ has been reported (see for example U.S. Pat. NO. 3,728,382).

SUMMARY OF THE INVENTION

The invention sought to be patented resides in the concept of a chemical compound of the structure:

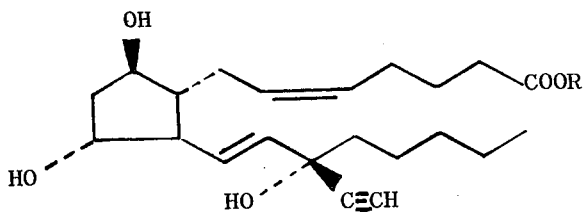

wherein R is hydrogen, alkyl of from 1 to 6 carbon atoms, an alkali metal cation, or a pharmacologically acceptable cation derived from ammonia or a basic amine.

The tangible embodiments of the compositions of the invention possess the inherent general physical properties of being clear to yellow oils, are substantially insoluble in water and are generally soluble in organic solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, and the mode of synthesis, confirm the structure of the compositions sought to be patented.

The tangible embodiments of the compositions of the invention possess the inherent applied use characteristic of exerting hypotensive and bronchodilating effects, upon administration to warm-blooded animals. These effects are evidenced by pharmacological evaluation according to standard test procedures.

The invention sought to be patented in a sub-generic composition aspect resides in the concept of a chemical compound of the structure:

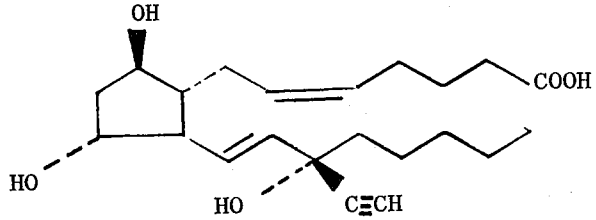

The tangible embodiment of the sub-generic composition aspect of the invention possesses the inherent general physical properties of being a clear to yellow oil, is substantially insoluble in water and is generally soluble in polar solvents such as ethyl acetate and ether. Examination of the compound produced according to the hereinafter described process reveals, upon infrared, nuclear magnetic resonance, and mass spectrographic analysis, spectral data supporting the molecular structure herein set forth. The aforementioned physical characteristics, taken together with the nature of the starting materials, and the mode of synthesis, confirm the structure of the composition sought to be patented.

The tangible embodiment of the sub-generic composition aspect of the invention possesses the inherent applied use characteristic of exerting hypotensive, and bronchodilating effects upon administration to warm-blooded animals. These effects are evidenced by pharmacological evaluation according to standard test procedures.

DESCRIPTION OF THE PREFERRED EMBODIMENTS

In order to designate the stereochemistry of the substituents on the prostaglandin skeleton, different types of lines are utilized when representing the bonds of said substituents. Thus, with reference to the plane of the paper, when a dashed line (----) is used, the substituent will be understood to be in the $\alpha$ (down) configuration, and when a heavy line ( ▶ ) is used, the substituent will be understood to be in the $\beta$ (up) configuration. For purposes of convenience, the prostaglandin molecules referred to in the following description are free carboxylic acids; however, it will be obvious to those skilled in the art that these free acids may readily be esterified as for example with diazomethane, or with an alkanol and the proper catalyst. These esters are considered to be full equivalents to the free acid for the purposes of the invention. Finally, the use of a specific embodiment in the following description to illustrate the invention is merely descriptive and is not intended to delimit the scope of the invention.

The starting material for the synthesis of the compounds of the invention is 15-oxo-PGF$_{2\beta}$ which may be prepared synthetically as described, for example, in U.S. Pat. No. 3,728,382. This compound, 15-oxo-PGF$_{2\beta}$, is reacted with an ethynyl metallic reagent such as ethynyl magnesium bromide, or lithium acetylide producing a mixture of the two tertiary alcohols 15$\alpha$-ethynyl-PGF$_{2\beta}$ and 15$\beta$-ethynyl-PGF$_{2\beta}$. This mixture is next separated by, for example, silica gel chromatography into pure 15$\alpha$-ethynyl-PGF$_{2\beta}$ and pure 15$\beta$-ethynyl-PGF$_{2\beta}$.

The compound of the invention which bears a carboxyl group can be readily converted to an alkali metal salt or a salt of a pharmacologically acceptable cation derived from ammonia or a basic amine. All such salts are full equivalents of the subject matter particularly claimed.

In using the compounds of the invention to produce bronchodilating effects in warm-blooded animals, they may be administered in a variety of dosage forms: oral, injectable, and aerosol inhalation. Aerosol inhalation is a preferred method because of its rapid onset of action, great potency, and specificity of action. The particular dosage to obtain the bronchodilating effect will vary with the particular compound employed, the particular animal involved, and the degree of bronchodilation desired. In the guinea pig, by aerosol inhalation, the dose to produce bronchodilation is from about 0.015 micrograms to about 50 micrograms, and preferably from about 0.015 to about 25 micrograms. The bronchodilation produced upon aerosol inhalation can be observed by the method of Rosenthale et al., J. Pharmacol. Exp. Ther., 178, 541 (1971). Using this procedure the following result was obtained.

| Compound | Dose (μg) | Percent Inhibition of the bronchoconstricting effects of a standard dose of acetylcholine |
|---|---|---|
| 7-(2β-[(3S)-3-Ethynyl-3-hydroxy-trans-1-octenyl]-3α,5β-dihydroxy-1α-cyclopentyl)-cis-5-heptenoic acid | 1.5 | 64 |
|  | 15 | 78 |

In the use of the compounds of the invention to produce hypotensive effects in warm-blooded animals, administration by the injectable route is preferred, preferably the intravenous route.

Thus in the anesthetized dog by the intravenous route the dose to produce hypotension is from about 1 μg/kg. to about 200 μg/kg. and preferably from about 10 μg/kg. to about 100 μg/kg. Using this procedure the following results were obtained.

| Compound | Dose (μg/kg) | Δb.p. (mm. Hg) |
|---|---|---|
| 7-(2β-[(3S)-3-Ethynyl-3-hydroxy-trans-1-octenyl]-3α,5β-dihydroxy-1α-cyclopentyl)-cis-5-heptenoic acid | 100 | −16 |

When used herein and in the appended claims, the term "alkali metal" includes, for example, sodium, potassium, lithium, and the like. A "pharmacologically acceptable cation derived from ammonia or a basic amine" contemplates the positively charged ammonium ion and analogous ions derived from organic nitrogenous bases strong enough to form such cations. Bases useful for the purpose of forming pharmacologically acceptable non-toxic addition salts of such compounds containing free carboxyl groups form a class whose limits are readily understood by those skilled in the art. Merely for illustration, they can be said to comprise, in cationic form, those of the formula:

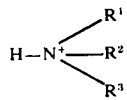

wherein $R^1$, $R^2$, and $R^3$, independently, are hydrogen, alkyl of from 1 to about 6 carbon atoms, cycloalkyl of from about 3 to about 6 carbon atoms, monocarbocyclicaryl of about 6 carbon atoms, monocarbocyclicarylalkyl of from about 7 to about 11 carbon atoms, hydroxyalkyl of from about 1 to about 3 carbon atoms, or monocarbocyclicarylhydroxyalkyl of from about 7 to about 15 carbon atoms or, when taken together with the nitrogen atom to which they are attached, any two of $R^1$, $R^2$, and $R^3$ form part of a 5 to 6-membered heterocyclic ring containing carbon, hydrogen, oxygen, nitrogen, said heterocyclic rings and said monocarbocyclicaryl groups being unsubstituted or mono- or dialkyl substituted, said alkyl groups containing from about 1 to about 6 carbon atoms. Illustrative therefore of R groups comprising pharmacologically-acceptable cations derived from ammonia or a basic amine are ammonium, mono-, di-, and tri-methylammonium, mono-, di-, and triethylammonium, mono-, di-, and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butylpiperidinium, 2-methylpiperidinium, 1-ethyl-2-methylpiperidinium, mono-, di- and triethanolammonium, ethyldiethanolammonium, n-butylmonoethanolammonium, tris-(hydroxymethyl)-methylammonium, phenylmonoethanolammonium, and the like.

The following example further illustrates the best mode contemplated by the inventor for the practice of the invention.

EXAMPLE 7-(2β-[(3R)-3-Ethynyl-3-Hydroxy-Trans-1-Octenyl]-3α,6β-Dihydroxy-1α-Cyclopentyl)-Cis-5-Heptenoic Acid (15α-Ethynyl-PGF$_{2β}$ ) and
7-(2β-[(3S)-3-Ethynyl-3-Hydroxy-Trans-1-Octenyl]-3α,5β-Dihydroxy-1α-cyclopentyl)-Cis-5-Heptenoic Acid (15β-Ethynyl-PGF$_{2β}$ )

Add a solution of 0.35 g. of 7-[3α,5β-dihydroxy-2β-(3-oxo-trans-1-octenyl)-1α-cyclopentyl]-cis-5-heptenoic acid in 15 ml. of tetrahydrofuran to a cooled solution of ethynyl magnesium bromide (prepared from 5.0 ml. of 3M methyl magnesium bromide and excess acetylene) in 50 ml. of tetrahydrofuran and stir for ½ hour. Dilute the reaction mixture with ammonium chloride solution, acidify with acetic acid and extract with ether. After washing and drying, evaporate the ether extract and chromatograph the residue on silica with 70% ethyl acetate in hexane to obtain 7-(2β-[(3R)-3-ethynyl-3-hydroxy-trans-1-octenyl]-3α,6β-dihydroxy-1α-cyclopentyl)-cis-5-heptenoic acid as an oil, $\lambda_{max}^{film}$ 3.0, 3.4, 5.75, 9.6, 10.2 μ. NMR: δ 5.3-6.1 (m, 4, olefinic H), 4.72 (3, 4, OH), 4.1 (m, 2, C-9, 11-H), 2.68 (s, acetylenic H) ppm. Mass spectrum: M+ at m/e 378.

Continue eluting the column with 90% ethyl acetate in hexane to obtain 7-(2β-[(3S)-3-ethynyl-3-hydroxy-trans-1-octenyl]-3α,5β-dihydroxy-1α-cyclopentyl)-cis-5-heptenoic acid as an oil, $\lambda_{max}^{film}$ 3.0, 3.45, 5.8, 9.6, 10.25 μ. Mass spectrum: M+ at m/e 378.

The subject matter which the applicant regards as his invention is particularly pointed out and distinctly claimed as follows:

1. A chemical compound of the structure:

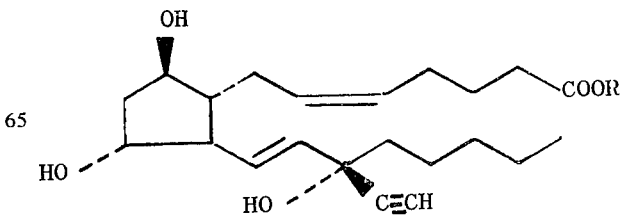

wherein R is hydrogen, alkyl of from 1 to 6 carbon atoms, an alkali metal cation, or a pharmacologically acceptable cation derived from ammonia or a basic amine.

2. The compound of claim 1 wherein R is hydrogen.

* * * * *